United States Patent [19]
Boffey et al.

[11] Patent Number: 5,580,768
[45] Date of Patent: Dec. 3, 1996

[54] METHOD FOR THE PRODUCTION OF PROTEINS IN PLANT FLUIDS

[75] Inventors: Stephen A. Boffey; Heddwyn Jones; Robert J. Slater, all of Hatfield, United Kingdom; Pappusamy Arokiaraj, Kuala Lumpur, Malaysia; Kay F. Cheong, Kuala Lumpur, Malaysia; Wan Y. Wan Abdul Rahaman, Kuala Lumpur, Malaysia; Hoong Y. Yeang, Kuala Lumpur, Malaysia

[73] Assignees: University of Hertfordshire, United Kingdom; The Board of the Rubber Research Institute of Malaysia, Malaysia

[21] Appl. No.: 153,099

[22] Filed: Nov. 17, 1993

[30]    Foreign Application Priority Data

Nov. 17, 1992 [GB] United Kingdom ............... 9224118

[51] Int. Cl.⁶ ..................... C12N 15/00; C12N 5/14; A01H 1/04
[52] U.S. Cl. ............. 435/172.3; 435/69.1; 435/240.4; 435/240.49; 800/205
[58] Field of Search ................... 800/205, DIG. 9; 435/69.1, 172.3, 240.4, 240.49, 35, 67

[56]            References Cited

FOREIGN PATENT DOCUMENTS

WO91/02066  2/1991  WIPO.

OTHER PUBLICATIONS

Chen et al (1982) Theor. Appl. Genet. 62(2) pp. 103–108.
Larkins et al (1985) J. Cell Biochem Suppl. 0 (9 part C).
Kush et al (1990) Proc. Natl. Acad Sci USA 87:1787–1790.
McCabe et al (1988) Bio/Technology 6:923–926.
Barton et al (1987) Plant Physiol 85:1103–1109.
Y. H. Song et al., *Acta Horticulturae*, 289, 261–262 (1991).
P. Goncalves et al., *Biological Abstracts*, BA75, Abstract No. 29105 (1982).
P. Arokiaraj et al., *J. Nat. Rubb. Res.*, 6(1), 55–61 (1991).
M. Kitayama et al., *Annual Meeting of the American Society of Plant Physiologists*, 93(1 Suppl.), 46, (1990) Abstract 261.
M. P. Asokan et al., *Biological Abstracts*, BA91, Abstract No. 61512 (1988).
W. R. Sharp et al. (Ed.), *Handbook of Plant Cell Culture*, vol. 2 (Crop Species), pp. 546–671, MacMillan Publishing Co.: New York (1984).
R. Backhaus et al., *J. Cell. Biochem.*, Suppl. O (13 Part D), 252 (1989).
I. El–Hadrami et al., *Annals of Botany*, 67, 511–515 (1991).
L. Lardet et al., *Compt. Rend. Acad. Sci. Paris*, 310(5), 195–202 (1990).
A. C. Dhar et al., *Plant Cell Reports*, 8(8), 489–492 (1989).

*Primary Examiner*—David T. Fox
*Assistant Examiner*—Elizabeth F. McElwain
*Attorney, Agent, or Firm*—Wenderoth, Lind & Ponack

[57]            ABSTRACT

A method of producing a genetically transformed fluid-producing plant comprises:
  i) inserting into the plant tissue a gene or gene fragment controlling the expression of a target product, and
  ii) regenerating a plant from said tissue, the genetically transformed plant being capable of expressing the target product in the fluid that it produces.

There are also provided clones of genetically transformed fluid-producing plants which contain in their cells a chromosomal insert such that the target product is expressed in the fluids that the plants produce. There is further described a method of producing a protein or other target product which comprises:
  i) harvesting the fluid from a genetically transformed fluid-producing tree or plant, or a clone thereof, and
  ii) recovering the target protein or other product from said fluid.

Most preferably, the plants are rubber (Hevea) plants and the genes are foreign genes that code for pharmaceutically valuable protein products which can be harvested in the latex produced by the plants.

5 Claims, 8 Drawing Sheets

1 2 3 4 5 6

1 2 3 4 5 6

METHOD FOR THE PRODUCTION OF PROTEINS IN PLANT FLUIDS

BACKGROUND OF THE INVENTION

This invention relates to a method of producing genetically transformed plants which are capable of expressing a desired gene product, and to clones of said genetically transformed plants having the same ability. More particularly, the plants concerned are of a type which produce a voluminous fluid and the target gene product is expressed in said fluid. Most preferably, the plants are rubber (Hevea) plants and the genes are foreign genes that code for pharmaceutically valuable protein products which can then be harvested in the latex produced by the plants and recovered therefrom.

Techniques for the genetic transformation of various microorganisms, such as yeasts, fungi and bacteria, for the purposes of producing specific proteins through the expression of "foreign" genes are well known. However, microorganisms require the maintenance of suitable conditions in which to survive and multiply. For example, the ambient temperature, pH value and aeration level usually need to be carefully controlled, while nutrients must be added to the culture medium in carefully regulated doses and waste products removed. Rigorous aseptic practices must be observed in order to avoid contamination by extraneous microbes. Microorganisms are thus normally cultured in sophisticated fermentors or bioreactors and which are housed in expensively maintained factories. Such overheads are reflected in the high price of the protein end-products.

More recently, attention has turned to the introduction of foreign genes into plants, such as tobacco plants. This application of genetic transformation techniques has allowed the incorporation of a variety of important genetic traits for crop improvement and also for the biotechnological production of extractable, valuable, foreign proteins (such as antibodies). Unlike microorganisms, plants tend to take care of themselves, requiring little more than sunlight, water and basic horticultural input, and can readily be cultivated on a cost efficient basis. Several different techniques have been developed to enable the introduction of foreign genes into various plant species and these include:
- the Agrobacterium vector system, which involves infection of the plant tissue with a bacterium (Agrobacterium) into which the foreign gene has been inserted. A number of methods for transforming plant cells with Agrobacterium are well known (Vancanneyt et al., 1990; Horsch et al., 1985; Bevan, 1984 and Herrera-Estrella et al., 1983);
- the biolistic or particle gun method, which permits genetic material to be delivered directly into intact cells or tissues by bombarding regenerable tissues, such as meristems or embryogenic callus, with DNA-coated microparticles. The microparticles penetrate the plant cells, acting as inert carriers of the genetic material to be introduced (Gordon-Kamm et al., 1990 and Sanford et al., 1987). Microprojectile bombardment of embryogenic suspension cultures has proven successful for the production of transgenic plants of yellow-poplar (Dayton et al., 1992) cotton (Finer and McMullen, 1990), maize (Gordon-Kamm et al., 1990) and soybean (McMullen and Finer, 1990). Various parameters that influence DNA delivery by particle bombardment have been defined (Klein et al., 1988; Wang et al., 1988);
- by imbibition of the foreign gene into the plant tissue (Simon, 1974); and
- electroporation.

When this approach is adopted, however, the recovery of the target product involves the harvesting and destruction of the entire plant or at least a substantial portion of the plant. Even where the plant is not totally destroyed, it then requires a lengthy period of recovery for re-growth before a further harvest is possible. In addition, the extraction of the protein product from plants such as tobacco (and indeed also from most of the microorganisms which are commonly used for such purposes) involves the homogenization of tissue solids. This can be a relatively problematic and inefficient operation.

The Brazilian rubber tree, *Hevea brasiliensis* Muell-Arg, belongs to the family Euphorbiaceae and has been commercially exploited for the production of natural rubber for about a century. There are in fact nine species in the genus Hevea, but *Hevea brasiliensis* is the most widely cultivated and commercially valuable since it gives the highest yield of latex.

Latex is traditionally extracted from rubber trees by a method known as "tapping". This can be achieved either by a bark excision technique, in which a strip of bark is cut out of the tree trunk so as to initiate latex flow (subsequent tappings being carried out by excising a thin layer of bark from the same cut), or by a bark incision technique, according to which one or more punctures are made into the bark to initiate the flow of latex. Tapping is thus a non-destructive method of latex recovery and which may be conducted repeatedly and at regular intervals, typically every alternate day. Natural rubber constitutes about a third of the latex and can be readily extracted by various separation techniques, such as centrifugation.

SUMMARY OF THE INVENTION

The rubber tree is almost unique in being able to produce a voluminous sap or exudate, i.e. latex, which can be continually harvested without any harmful effect. The present inventors have utilised this property of the rubber tree, together with genetic engineering techniques, to provide a new and advantageous route for the production of pharmaceutically valuable proteins and other target products.

According to the present invention there is provided a method of producing a genetically transformed fluid-producing plant which comprises:
  i) inserting into the plant tissue a gene or gene fragment controlling the expression of a target product, and
  ii) regenerating a plant from said tissue, the genetically transformed plant being capable of expressing the target product in the fluid that it produces.

According to a further embodiment of the present invention there is provided a plant clone which contains in its cells a chromosomal insert that includes a promoter and a gene or gene fragment controlling the expression of a target product, such that said target product is expressed or is capable of being expressed in the fluid that it produces.

In a particularly preferred embodiment, the invention provides a Hevea plant clone which contains in its cells a chromosomal insert that includes a promoter and a gene or gene fragment controlling the expression of a target product, such that said target product is expressed or is capable of being expressed in the latex.

The present invention further provides a method of producing clones of the aforementioned types which comprises bud grafting, taking a cutting or otherwise performing vegetative propagation of a suitably genetically transformed plant.

In a still further embodiment, the present invention provides a method of producing a protein or other product which comprises:

i) harvesting the fluid from a genetically transformed fluid-producing tree or plant, or a clone thereof, and ii) recovering the target protein or other product from said fluid.

The method is applicable to all species of Hevea, and references herein to Hevea plants and trees are to be understood accordingly, but *Hevea brasiliensis* is particularly preferred.

Hevea plants are well suited for use in the present invention since the fluid that they produce (i.e. latex) is easy to harvest non-destructively, easy to process and is naturally protein-rich (and therefore amenable to foreign protein production in the transgenic plant). It is to be understood, however, that other plants which produce (i.e. retain or exude) a voluminous fluid or sap are also suitable for use in this invention. Examples include:

- the Agave plant. Some varieties can produce up to a liter of exudate a day from their hollowed-out pith;
- the coconut palm. Its inflorescence can be tapped to induce a copious flow of exudate;
- plant organs that do not exude but nevertheless retain considerable volumes of fluid. For instance, the liquid endosperm of the young coconut fruit (i.e. the "water" or "milk") can be harvested in large quantities.

The approach underlying this invention falls into three main stages:

i) The process of genetic transformation of the plant, whereby the DNA molecule representing the gene that codes for the target protein or other product is inserted into the genetic complement of tissues of the plant. It will be appreciated that the gene will also need to be accompanied by a promoter. While so-called "universal" promoters (which are not tissue specific and generally turn on gene expression in all tissues of the plant, including the sap or fluid) may be employed, the promoter is more preferably fluid-specific. In the case of the rubber plant, the promoter is most preferably latex-specific.

Various techniques are known for introducing genes into plants, as acknowledged above, and any of these may be employed. Particularly preferred are the Agrobacterium vector system, that involves infection of the tissue with an Agrobacterium into which the desired gene has already been inserted, and the biolistic or particle gun method, according to which the desired gene is propelled into the tissue on a microparticle. Plant tissue that bears the inserted gene or gene fragment is known as transformed or transgenic tissue. In the case of the rubber plant, the transformation is performed on anther derived callus tissue taken from the staminal column of a flower on the Hevea plant.

The promoter and gene or gene fragment introduced by the transformation technique may be either native or foreign to the plant concerned. It is possible to enhance the expression of a native gene by modifying the promoter or by inserting multiple copies of that gene. Foreign genes may be introduced which code for a variety of protein-based products, most preferably pharmaceutically valuable protein products.

ii) The regeneration of a plant from the transformed tissue, the planting out and nurturing to maturity. For example, through the technique of tissue culture the transformed callus tissue of Hevea is regenerated, via an embryo stage, into a plantlet which is transgenic and bears the inserted gene in its genetic complement. In time, the plantlet matures into a full grown transgenic rubber tree and the target protein or other product expressed by the inserted gene is present in its latex.

iii) The harvesting of the target protein or other product in the fluid produced by the plant or tree and recovering the same therefrom. In the case of Hevea, the fluid harvested will of course be latex. Once the transgenic rubber plant has grown to sufficient maturity, usually after from two to five years, it is tapped and the latex harvested at regular intervals. The latex is then usually centrifuged so as to separate out the natural rubber, the aqueous C-serum and the so-called "bottom fraction". The target protein or other product may be contained in any part of the latex and can be extracted and purified by conventional means (such as preparative column chromatography). Preferably, it is present in the C-serum or in the bottom fraction, the latter comprising mainly lutoids and which are membrane-bound vesicles containing their own serum (B-serum). The B-serum can be released from lutoids by rupturing their membranes using detergents, such as Triton X-100, or by alternate freezing and thawing. Any of the target protein or other product that may be bound to biological membranes in the latex can be recovered by solubilising with detergents such as sodium dodecyl sulphate.

The present invention provides a new and advantageous route for the synthesis of a wide range of proteinaceous and non-proteinaceous products. It is particularly suited to the production of pharmaceutically valuable protein products. In principle, the technique should be applicable to the synthesis of virtually any protein-based product provided that the gene coding for its expression is known. It will be appreciated that the protein product which is directly coded for by the inserted gene may itself catalyse, within the plant, the production of a different end-product. The latter (proteinaceous or non-proteinaceous) product may then be harvested as the commercially valuable end-product. Examples of products that may be produced by the transgenic plants or trees are as follows:

(a) Insulin for diabetes treatment (b) Blood-clotting factors for haemophilia treatment (c) Blood clot-dissolving activators for cardiac treatment (d) Tumor necrotic factor for cancer treatment (e) Erythropoietin for anaemia treatment (f) Viral coat proteins for vaccine production (g) 'PHB', a plastic similar to polypropylene and which is used for the manufacture of bottles, wrappings, etc.

The use of rubber trees in particular in the present invention has a number of significant advantages, of which the following are especially noteworthy:

- Production is continual, since the latex containing the target protein or other product is harvested at regular intervals, and product recovery is simple. As latex is a fluid, recovery of the target product does not involve tissue homogenisation.

- The approach is environment-friendly. The process is driven by the sun and is thus energy efficient and essentially pollution-free.

- Rubber trees require no special attention beyond routine horticultural maintenance. Their use is thus highly cost-efficient.

- The technique is applicable for use for a wide range of target products.

- The latex that flows out of the rubber tree is completely free of bacteria and animal viruses. This is in contrast to the rigorous aseptic practices which need to be adopted when genetically transformed microorganisms or animals are employed.
- Rubber trees are amenable to clonal or vegetative propagation, most commonly by bud grafting. Other approaches include taking a cutting, marcotting or tissue culture. Thus, an unlimited number of genetically identical plants (clones) can be generated from a single transgenic plant—all of which will go on to express the desired product in their latex.
- Rubber trees have an economic life of about thirty years. During this time, in addition to producing the target product, the genetically transformed tree will of course continue to produce natural rubber in its latex and which is a valuable commodity in its own right. When it is eventually felled, the tree also yields a valuable tropical timber (rubberwood) which is much sought after for export and furniture manufacture.

Some of these advantages are shared by other fluid-producing plants suitable for use in this invention.

BRIEF DESCRIPTION OF THE DRAWINGS

FIG. 6B(2) depicts roots regenerated from transformed embryoids.

DESCRIPTION OF THE PREFERRED EMBODIMENTS

Figure 1B:
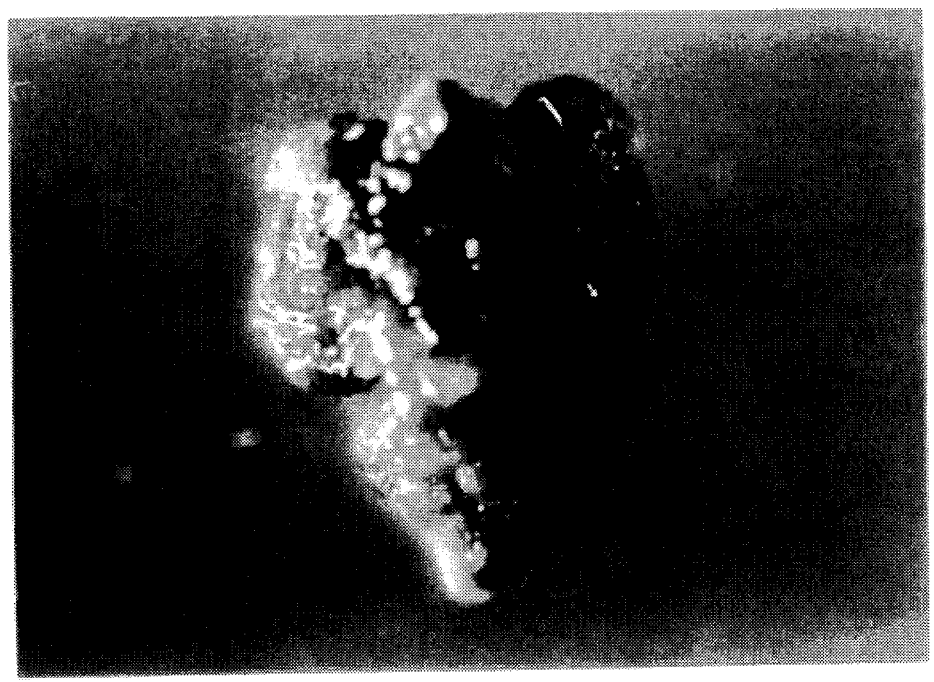
FIGS. 1A–1D depict GUS activity in Hevea tissue after treatment with chromogenic substrate X-gluc.
Figure 1A:
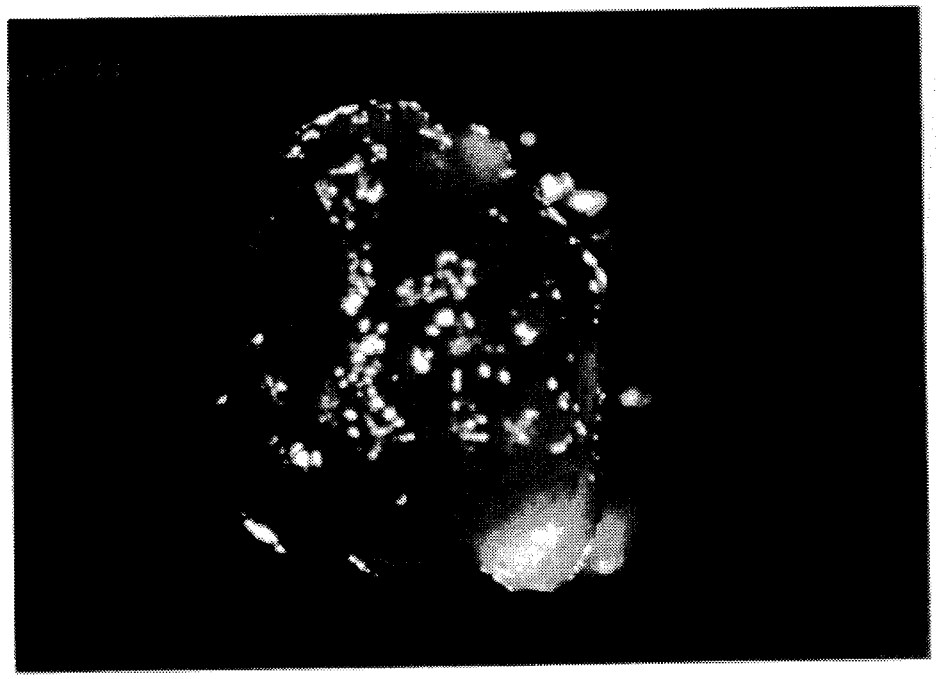
Figure 1D:
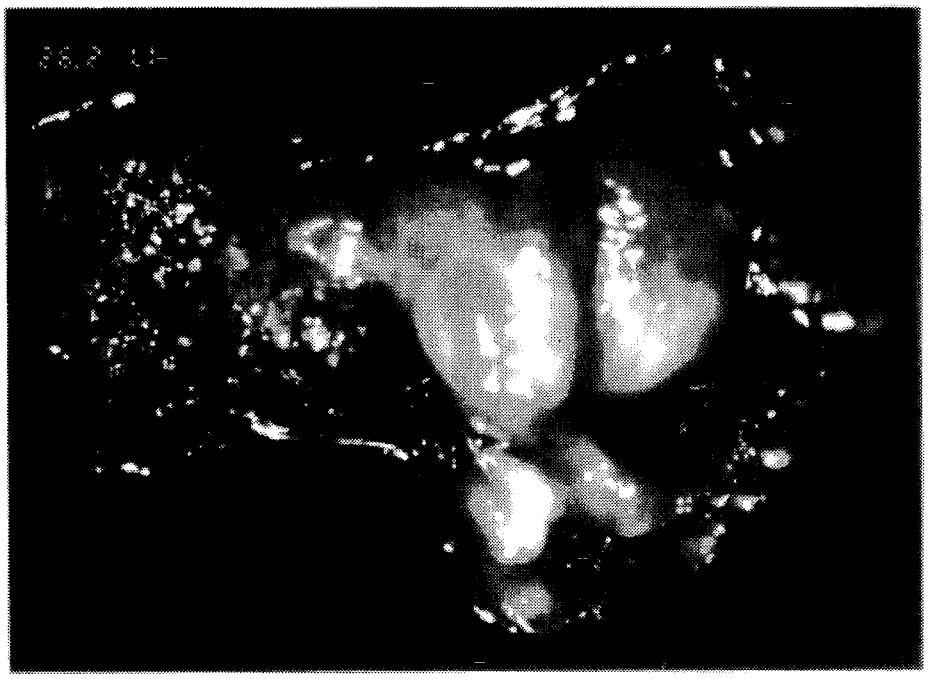
Figure 1C:
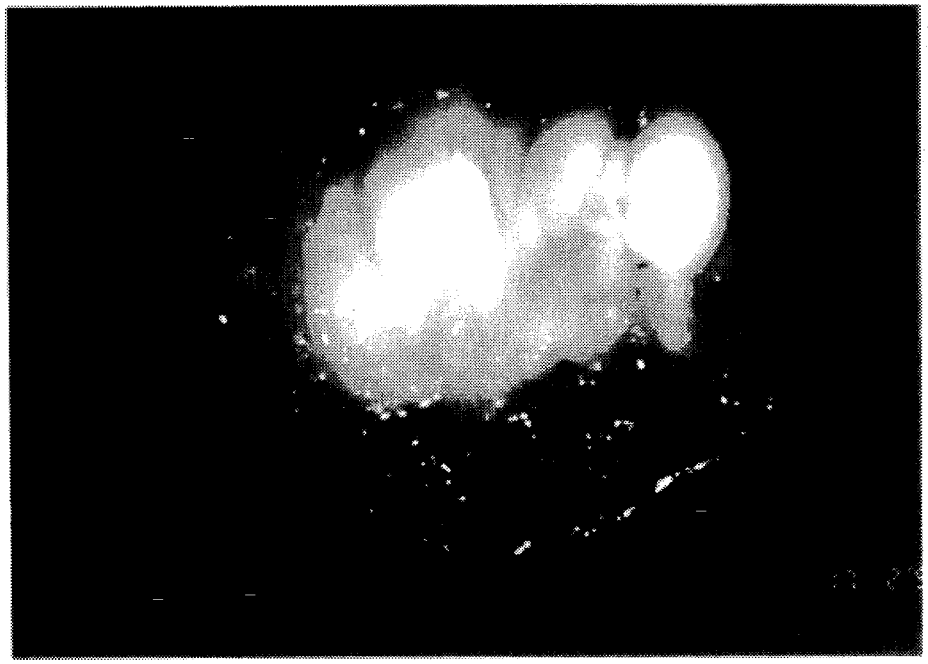

This invention will now be illustrated further by the following Examples. Example 1 relates to the genetic transformation of *Hevea brasiliensis* using the particle gun method, while Examples 2 and 3 show the use of the Agrobacterium vector system and the imbibition technique, respectively. The enzyme glucuronidase is used as an example of the target protein, but the same procedures will generally apply for other products with the gene controlling the production of glucuronidase being substituted by the appropriate gene for the target protein. The following abbreviations are quoted in the Examples:

MB=Hevea anther culture initiation medium
GUS/gus=β-glucuronidase
NPTII/nptII=neomycin phosphotransferase
CAT/cat=chloramphenicol acetyl transferase
PCR=polymerase chain reaction
ELISA=enzyme linked immunosorbent assay
CaMV=cauliflower mosaic virus

EXAMPLE 1

Plant Material and Tissue Culture

Embryogenic Hevea anther callus was initiated from individual anthers of the staminal column. The callus was initiated and maintained at 25° C. on MB medium (Chen et al., 1984) and was used for transformation after four weeks on this medium. All the tissue culture procedures essentially followed the protocol described in Chen et al. (1984).

Plant Expression Vectors

The following plasmids were used for transformation: pBI221.1 (Jefferson, 1987) containing the β-glucuronidase (gus) gene, pMON9793 (Gasser, Monsanto Company, unpublished) containing the gus and nptII genes, pDE10 (Rhodes, Norwich, UK) containing the cat and nptII genes and pHP23 (Paszkowski and Saul, 1988) containing nptII. These genes were under the control of the strong CaMV 35S promoter. Recombinant plasmids were grown in *E. coli*, isolated by alkali lysis and purified by caesium chloride/ethidium bromide density gradient centrifugation (Sambrook, Fritsch and Maniatis, 1989). Plasmid DNA was quantified by its absorbance at 260 nm and by gel electrophoresis.

Microprojectile Bombardment

Plasmid DNA was precipitated onto tungsten particles as described previously (Gordon-Kamm et al., 1990). The precipitation mixture included 130 mg tungsten particles, 25 µg plasmid DNA, 1.1M $CaCl_2 \cdot 2H_2O$ and 8.7 mM spermidine in a total volume of 575 µL. After addition of components in the above order, the mixture was vortexed at 4° C. for 10 minutes, centrifuged at 500×g for 5 minutes, and then 550 µL of supernatant were discarded. The pellet was resuspended in the remaining 25 µL of supernatant and, from this, 1 µL of the tungsten suspension was loaded onto a microprojectile and accelerated toward the target with a biolistic particle gun (Spearline Precision Engineering Ltd., UK). The anther calli were placed in the centre of a Whatman No 1 filter paper disc (7 cm) which was then positioned in the centre of a plastic petri dish (9 cm diameter) containing MB medium prior to bombardment. The callus cultures were positioned 5 cm below the microprojectile stopping plate, and a 100-µm mesh stainless steel screen was placed halfway between the stopping plate and the tissue to aid the dispersion of the tungsten particles. Each plate was bombarded once and the calli were then incubated for a short while in a growth chamber at 25° C. in the dark.

Selection of transformants

After post-bombardment incubation at 25° C. in the dark, calli were gently removed from the filter paper and placed on a fresh plate containing MB medium and further incubated for 10 days at 25° C. in the dark. Bombarded calli and controls were then transferred to MB selection medium containing 100 µg kanamycin sulphate $mL^{-1}$. Antibiotic resistant colonies were isolated four weeks after bombardment and transferred to differentiation medium containing 100 µg kanamycin sulphate $mL^{-1}$ and incubated at 25° C. in the light (250 µE $m^{-2}s^{-1}$). This stimulated the development of shoots and roots; however, even without antibiotic selection only a small percentage (3%) of the somatic embryos differentiate into plantlets (Chen et al., 1981 b).

Enzyme Assays

NPTII: NPTII activity in transformed tissue was determined using an ELISA kit (5 Prime–3 Prime, Inc., obtained through CP Laboratories, UK). Approximately 400 µg of extracted protein were used per assay.

GUS: Histochemical analysis of β-glucuronidase activity in transformed anther callus, embryoids and roots of Hevea was performed using the substrate 5-bromo-4-chloro-3-indolyl glucuronide (X-gluc) according to the protocol of Jefferson (1987). Tissue was examined for blue stained cells 18–36 hours after the addition of X-gluc. Photomicrographs were taken using a Nikon SZM-U 1:10 zoom binocular microscope with Kodacolor Tungsten 160T film. Fluorometric assay of GUS activity was performed using the substrate 4-methyl-umbeliferyl-beta-D-glucuronide (Jefferson et al., 1987).

CAT: CAT activity was determined as described by Gorman et al., 1982. Positive controls were run in parallel with bombarded tissue samples using 1 unit of bacterial CAT enzyme (Sigma). Negative controls included samples of the CAT buffer and extracts from non-bombarded embryoids.

DNA Isolation and PCR

DNA isolation: Genomic DNA was isolated using the Protease Method as described by Draper et al,, (1988). Fifty mg of lyophilised Hevea tissue were ground to a fine powder using a pestle and mortar. The powdered tissue was then mixed thoroughly with 400 µL of protease buffer (100 mM Tris-HCl pH8.5, 100 mM NaCl, 50 mM EDTA pH8.0, 2.0% SDS, 0.1 mg Proteinase K mL$^{-1}$) and incubated at 37° C. for 1–2 hours with occasional gentle inversion. The tissue/buffer homogenate was extracted with 80 µL of phenol and 80 µL of 24:1 (v/v) chloroform/isoamylalcohol. The aqueous phase was separated by centrifugation and the extraction procedure repeated. The collected aqueous phase after the second extraction was precipitated overnight at −20° C. using 0.54 volumes of isopropanol. The following day, the precipitate was washed with 70% ethanol and resuspended in 50 µL TE buffer (10 mM Tris-HCl pH 8.0, 1.0 mM EDTA pH 8.0). For restriction of Hevea genomic DNA, 2 µL of 10×BSA/spermidine (2.5 mg BSA mL$^{-1}$, 40 mM spermidine) were routinely included in the restriction buffer to overcome problems due to the presence of impurities.

PCR: Each PCR reaction was carried out in 50 µL containing 10 mM Tris-HCl pH 8.8, 50 mM KCl, 1.5 mM MgCl$_2$, 50 µL mineral oil, 200 µM dATP, 200 µM dTTP, 200 µM dCTP, 200 µM dGTP, Taq polymerase (0.5–1.0 U), DNA (2–10 ng) and oligonucleotide primers: 5' GGTGG-GAAAGCGCGTYACAAG 3' and 5' GTTTACGCGTTGC-TYCCGCCA 3' (positions 400–420 and 1599–1579 respectively in the GUS gene, Jefferson et al., 1986). 100 ng of each primer were used in the PCR reaction. Taq polymerase was obtained from Amersham International pic. The denaturation temperature was 92° C. (duration 1 minute), annealing temperature was 55° C. (duration 1.5 minute) and extension temperature was 72° C. (duration 2.0 minute). The reactions were programmed for 30 cycles, using a programmable thermal controller (The Hybaid Thermal Reactor). DNA was detected after running samples on 1.0% agarose/ethidium bromide gels using TBE (0.9M Tris-HCl, 25 mM EDTA, 0.9 mM H$_3$BO$_3$) as running buffer.

RESULTS

Transformation and Regeneration

The biolistic protocol adopted followed the procedure established for the introduction of genes into barley embryos for studying transient gene expression (M. G. K. Jones, Rothamsted, U.K.). For particle bombardment the anther callus used was derived from a highly embryogenic Hevea clone (clone GL1). Upon transferring the bombarded callus onto selection medium, kanamycin resistant microcalli appeared to grow very slowly, however, these transformed calli appeared healthy and white among the dark and dying non-bombarded calli (FIG. 1). The percentage of antibiotic selected calli and embryoids showing blue coloration upon adding X-gluc reached 90% in callus and 80% in embryoids after bombardment using plasmid pMON9793. Using pB1221.2, but without kanamycin selection, the percentage of blue coloration reached 60% in callus and 70% in the embryoids (Table 2). The higher transfer efficiency exhibited in callus and embryoids bombarded using plasmid pMON9793 is probably due to kanamycin selection.

TABLE 2

Percentage of callus and embryoids expressing GUS activity

| | |
|---|---|
| Plasmids | 10 |
| Transformants | 10 |
| No of calli | 9 |
| No's of calli expressing GUS | 8 |
| Percentage | 90 |
| pMON9793 | 10 |
| anther callus | 10 |
| embryoids | 6 |
| pBI221.2 | 7 |
| anther callus | 60 |
| embryoids | 70 |

The histochemical assay for GUS often demonstrated a heterogeneous pattern of enzyme activity in callus maintained without kanamycin selection, but exhibited a homogeneous pattern in cells after kanamycin selection. None of the control (non-bombarded) anther callus, embryoids or roots were stained blue when using X-gluc. The results of these experiments are summarized in photomicrographs shown in FIG. 1.

Figure 2:
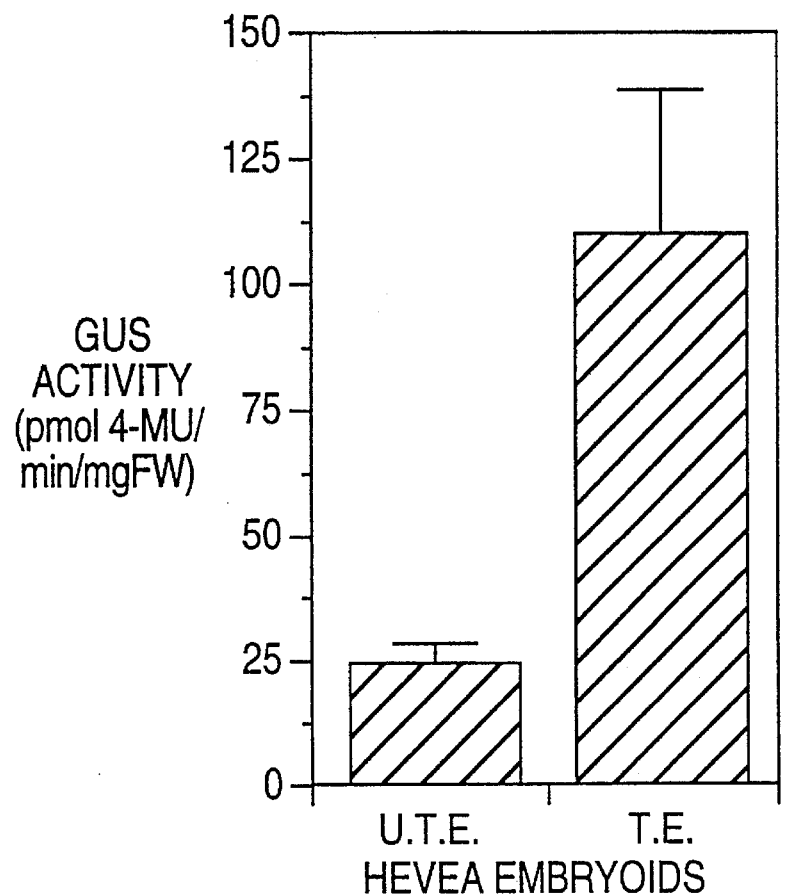
FIG. 2 is a bar chart showing GUS activity in bombarded Hevea embryoids (T.E.) compared with control values (U.T.E.).

The results obtained from histochemical staining for GUS activity were confirmed using a fluorometric assay (FIG. 2). GUS fluorometric activity was evident in 90% of the transformed embryoids analysed and, overall, there was a 4-fold increase in GUS activity in transformed embryoids compared with non-bombarded control values.

Figure 3:
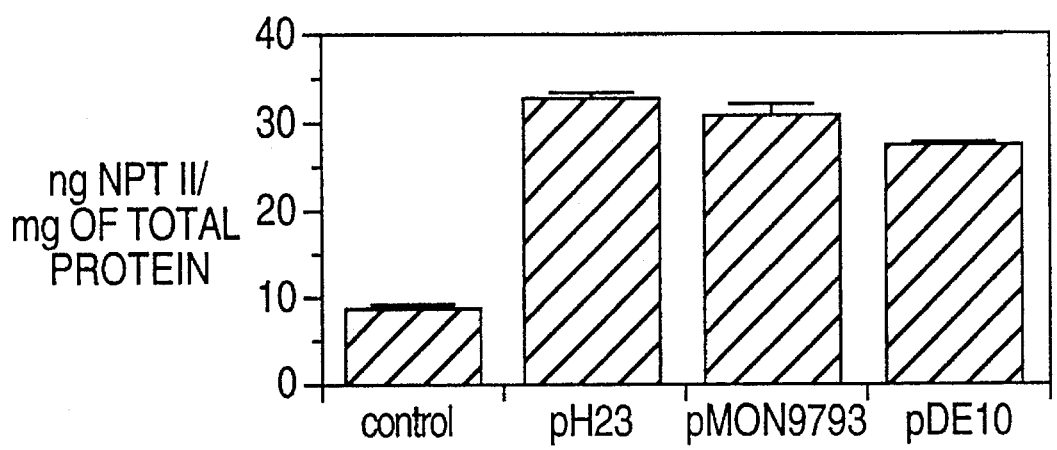
FIG. 3 depicts NPT II protein levels in bombarded Hevea callus compared with control values.

NPT II levels were quantified in transformed calli using the ELISA technique (FIG. 3). Overall, NPT II protein levels were approximately four-fold above background control values and ranged from 28 to 32 ng NPT II per mg total protein.

Figure 4:
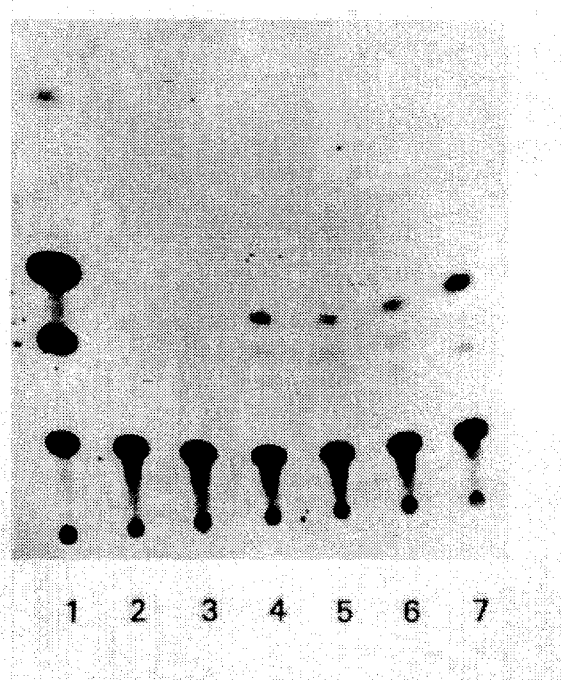
FIG. 4 depicts an autoradiograph showing CAT activity in Hevea tissue previously bombarded with plasmid pDE10.

In addition to the use of gus as a reporter gene, we also used a cat gene to monitor gene delivery into Hevea. The results for these experiments are summarised in the autoradiograph shown in FIG. 4. It is clear that plasmids containing the cat gene can be delivered by bombardment and are efficiently expressed in Hevea callus and embryoid tissue. Only a very low level of CAT activity was observed in the non-bombarded control tissues (FIG. 4, lane 3).

Figure 5:
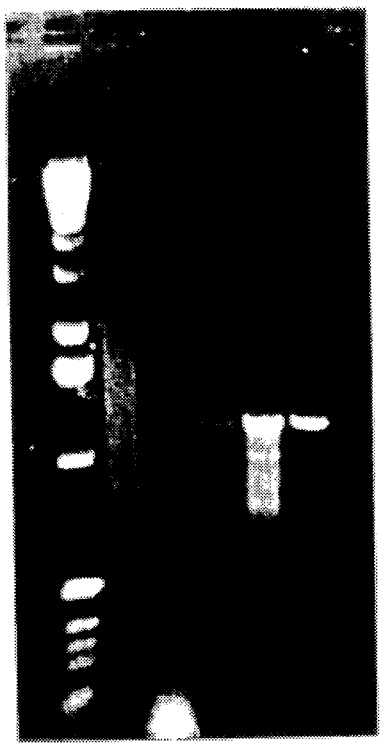
FIG. 5 depicts amplification of the gus gene from DNA isolated from x week old antibiotic selected callus of Hevea.

A direct check for the presence of transferred reporter genes in Hevea callus was performed using the PCR technique. The method of Hamill et al. (1991) was used to amplify the internal sequence of gus. After 30 cycles of amplification a single band was visible on agarose/ethidium bromide gels using as little as 0.8 ng template DNA (FIG. 5). This amplified band was identical in size to the gus gene.

Figure 7:
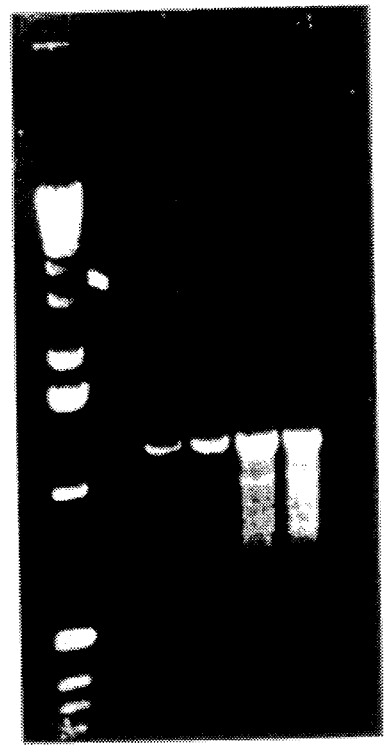
FIG. 7 depicts the detection of gus gene by PCR of genomic DNA isolated from a regenerated *Hevea brasiliensis* plantlet.

Finally, we managed to regenerate two Hevea plantlets (axenically grown) after particle bombardment (FIG. 6). The plantlets appeared quite normal and the roots were stained blue after treatment with X-gluc. The presence of the gus gene in one of these plantlets was confirmed using the same PCR protocol performed on DNA derived from callus. As shown in FIG. 7, successful amplification of the gus gene was achieved with as little as 4.0 ng of Hevea leaf DNA. We could not amplify the gus gene in any of the control (non-bombarded) callus, embryoids or plantlets using the same PCR conditions as described above.

These results show that microprojectiles/microparticles can deliver foreign DNA into the cells of *Hevea brasiliensis*, as determined by reporter gene assays, the recovery of Kanamycin-resistant transformants and the use of the PCR technique. The DNA carried into the cell apparently desorbs from the surface of the microprojectile and is transported by some passive or active mechanism into the nucleus where its genes may be expressed.

EXAMPLE 2

I. Callus Tissue Transformation

Male flowers of selected Hevea cultivars were disinfected with Chlorox (5.25% a.i. sodium hypochlorite) for five minutes followed by several washes with sterile distilled water. The anthers were excised from the staminal column and inoculated on MB medium (20 anthers/petri plate). The cultures are incubated at 25° C. in the dark.

Genetic transformation via Agrobacterium

Four week old Hevea anther callus was infected with *Agrobacterium tumefaciens* that bears the genes for the enzymes glucoronidase (GUS) and neomycin phosphotransferase. The latter confers resistance to the antibiotic kanamycin. The callus was immersed in an overnight culture of *Agrobacterium tumefaciens* suspension, pH 5.8, for one minute, diluted with liquid MB medium containing 7% sucrose but without hormone supplementation, to give a final estimated bacterial population of $3.7 \times 10^8$ cells/ml. Estimation of population density was carried out by measuring absorbance at 600 nm of the overnight culture. The excess bacterial suspension was blotted from the callus using sterile Whatman No. 1 filter paper, and the latter was transferred to the petri plate for a co-cultivation period of two days.

The callus was transferred to MB medium containing the antibiotics cefotaxime (250 µg/ml) and Ticar (500 µg/ml) to kill off the Agrobacterium.

After one week, the callus was placed on selective plates (MB, Km 100 µg/ml) but still maintaining cefotaxime and Ticar. The concentrations of cefotaxime and Ticar were gradually reduced in subsequent sub-cultures at weekly intervals.

II. Regeneration of the transformed plantlet

The callus culture was plated on MB medium and incubated for a period of one week and then transferred to fresh medium (MB) every seven days. After three weeks, the culture was transferred to selective differentiation medium. This phase lasts approximately 2 months, with transfers carried out to fresh medium after 30 days. Cultures were again incubated in the dark at 25° C. Both the initiation medium (MB) and the differentiation medium contained kanamycin sulphate (100 µg/ml) to select for the transformed cells.

After a period of about 60 days in the differentiation medium, the developed embryoids were transferred to the developmental medium for the formation of shoot and roots. The plantlet was planted out in the soil and can then be nurtured to maturity.

Figure 8A:
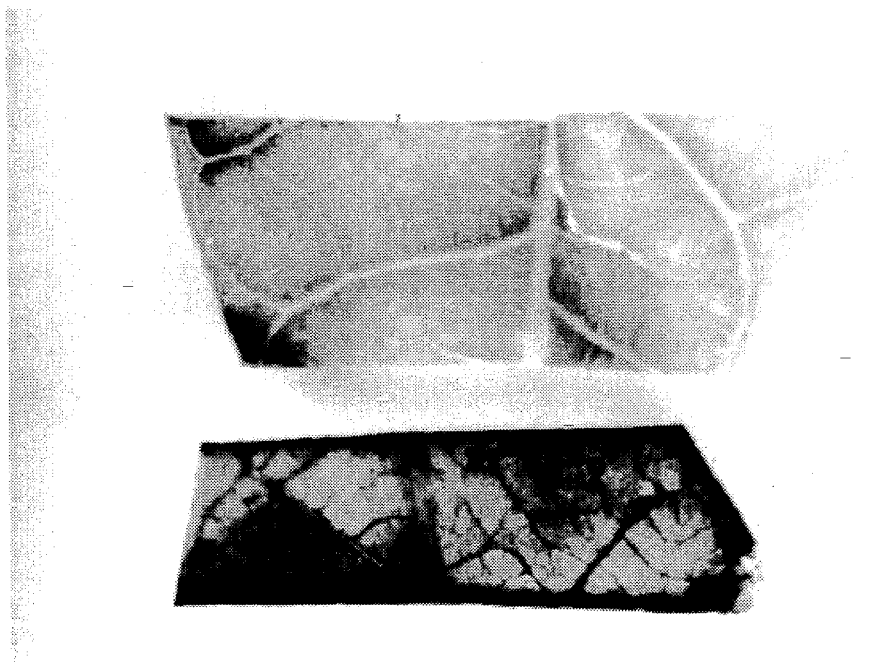
FIG. 8A depicts surface of leaf samples incubated in X-gluc.
Figure 8B:
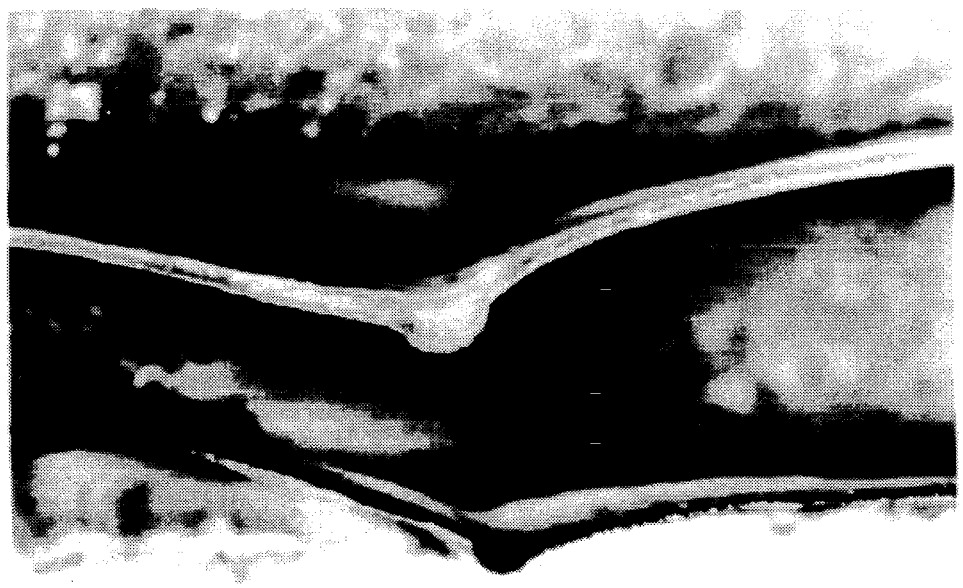
FIG. 8B depicts sections of leaf samples incubated in X-gluc.

*Hevea brasiliensis* plantlets have been successfully regenerated after insertion of the GUS gene by Agrobacterium mediation. The plantlets appeared normal and samples of the leaves were stained blue after treatment with X-gluc, indicating expression of the GUS gene. Samples of leaves from in vitro-cultured Hevea plants that were not transformed were unstained when similarly treated with X-gluc. The results are shown in FIGS. 8A and 8B.

EXAMPLE 3

The procedure of Example 2 was essentially followed except that, instead of the Agrobacterium vector system, the genetic transformation was performed by imbibition as follows:

Four week old Hevea anther callus was dehydrated by placing the tissues in a 37° C. incubator for 30 minutes. The callus was imbibed for 30 minutes in a DNA solution containing the gene for glucoronidase (100 µg of pBI221.1 DNA in sterile water). The culture was transferred to MB medium and subsequently to a differentiation medium. Unlike Example 2, however, the media did not include kanamycin sulphate.

LEGENDS TO FIGURES

FIG. 1. GUS activity in Hevea tissue after treatment with the chromogenic substrate X-gluc. (A) Control callus. (B) Cells from a 3 week old bombarded anther callus. (C) Control embryoid. (D) Embryoids after particle bombardment. All photographs are magnified ×25.

FIG. 2. A bar chart showing GUS activity in bombarded Hevea embryoids (T.E.) compared with control values (U.T.E.). The results are presented as mean±s.d.; n=20 embryoids.

FIG. 3. NPT II protein levels in bombarded Hevea callus compared with control values. The results are presented for 3 different plasmids (see methodology) harbouring the npt II gene. The values are presented as mean±s.d.; n–x replicates.

FIG. 4. Autoradiograph showing CAT activity in Hevea tissue previously bombarded with plasmid pDE10.

The positions of [$^{14}$C] chloramphenicol (CAP), [$^{14}$C] 1-acetylchloramphenicol (1-CAP), and [$^{14}$C] 3-acetylchloramphenicol (3-CAP) are indicated. Lane 1: commercial CAT (Sigma) used as positive control. Lane 2: negative control (containing only buffer). Lane 3: control (non-bombarded) anther callus. Lanes 4–6: different transformed anther calli three weeks after selection on kanamycin sulphate. Lane 7: embryoid tissue regenerated from bombarded callus in the presence of kanamycin sulphate.

FIG. 5. Amplification of the gus gene from DNA isolated from x week old antibiotic selected callus of Hevea. Lane 1: 1 kb ladder. Lane 2: 500 ng DNA. Lane 3: 100 ng DNA. Lane 4: 20 ng DNA. Lane 5: 4 ng DNA. Lane 6: 0.8 ng DNA.

Figure 6A:
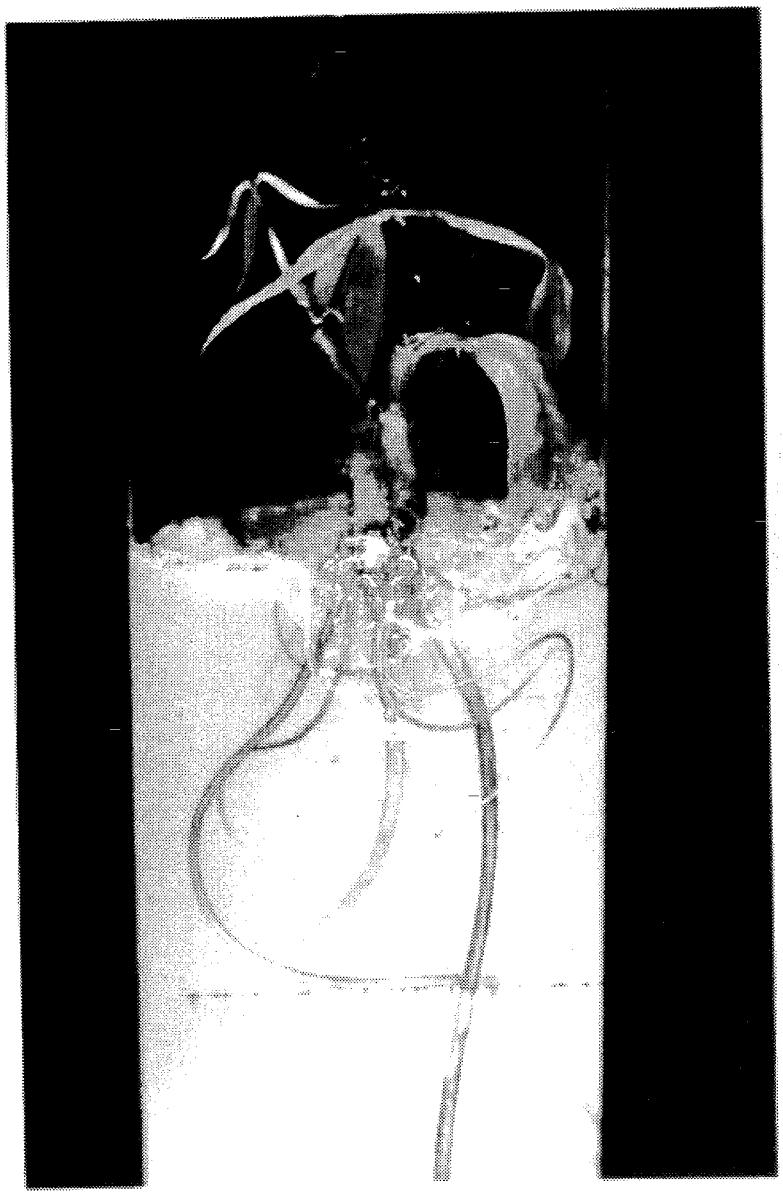
FIG. 6A depicts Hevea plantlet grown from the particle bombarded tissue shown in FIG. 1.
Figure 6B:
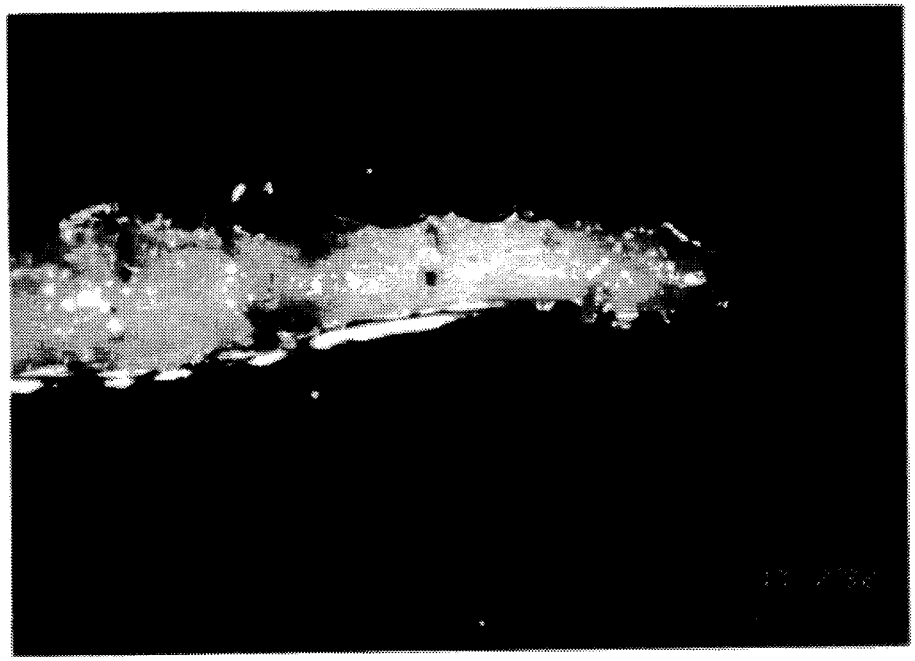
FIG. 6B(1) depicts the control root.
Figure 6C:
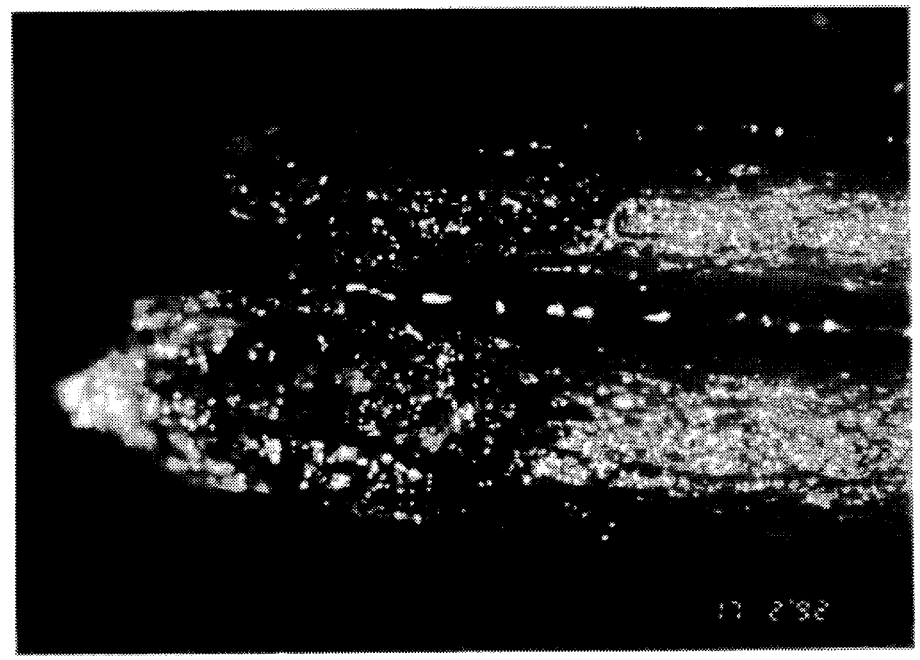

FIG. 6A. Hevea plantlet grown from the particle bombarded tissue shown in FIG. 1. GUS activity after treatment with the chromogenic substrate X-gluc. FIG. 6B. Control root. FIG. 6C. Roots regenerated from transformed embryoids. All photographs are magnified ×25.

FIG. 7. Detection of the gus gene by PCR of genomic DNA isolated from a regenerated *Hevea brasiliensis* plantlet. Lane 1: 1 kb ladder. Lane 2: 4.0 ng DNA from a control (non-bombarded) plant. Lane 3: 4.0 ng DNA from a transformed callus. Lane 4: 4.0 ng DNA from a transformed embryoid. Lane 5: 4.0 ng DNA isolated from a single leaf of a transformed Hevea plantlet.

FIG. 8A. Surfaces of leaf samples incubated in X-gluc. The untransformed sample (top) is unstained; while the transformed sample (below) is stained blue. The photograph is magnified ×10. FIG. 8B. Sections of leaf samples incubated in X-gluc. The untransformed sample (top) is unstained; while the transformed sample (below) is stained blue. The photograph is magnified ×31.

LITERATURE CITED

Chen Z (1984). Rubber (Hevea) In: Sharp W R, Evans D A, Ammirato P V and Yamada Y (eds). Handbook of plant cell culture, Vol 2: Crop species, Macmillan, New York: 546–571.

Dayton W H, Richard B M and Scott A M (1992). Expression of foreign genes in transgenic Yellow-Poplar plants. Plant Physiol. 98: 114–120.

Draper D, Scott R, Armitage P and Walden R (1988). In: Plant Genetic Transformation and Gene Expression—A Laboratory Manual.

Finer J J and McMullen M D (1990). Transformation of cotton (*Gossypium hirsutum* L.) via particle bombardment. Plant Cell Rep. 8: 586–589.

Gordon-Kamm W J, Spencer T M, Mangano M L, Adams T R, Daines R J, Start W G, O'Brien J V, Chambers S A, Adams W R, Willets N G, Rice T B, Mackey C J, Krueger R W, Kausch A P and Lemaux P G (1990). Transformation of maize cells and regeneration of fertile transgenic plants. Plant Cell 2: 603–618.

Gormon C M, Moffat L F and Howard B H (1982). Mol. Cell. Biol. 2: 1044–1051.

Hamill J D, Rounsley S, Spencer A, Todd G and Rhodes M J C (1991). The use of polymerase chain reaction in plant transformation studies. Plant Cell Reports 10: 221–224.

Harris R R, DeRobertis G A, Pierce D A, Moynihan M R and Everett N P (1990). Heterogeneity of x-gluc staining in transgenic maize callus (abstract). In Vitro Cell Dev. Biol. 26 (part II): 69.

Jefferson R A (1987). Assaying chimaeric genes in plants: The GUS gene fusion system. Plant Molec. Biol. Reporter 5: 389–405.

Jefferson R A, Burgess S M and Hirsh D (1986). Beta glucuronidase from *E. coli* as a gene fusion marker. Proc. Natl. Acad. Sci. USA 86: 8447–8451.

Jefferson R A, Kavanagh T A and Bevan M W (1987). GIS fusions: beta glucuronidase as a sensitive and versatile gene fusion marker in higher plants. EMBO J 6: 3901–3902.

Klein T M, Fromm M E, Weissinger A, Tomes D, Schaaf S, Sietten M and Sanford J C (1987). Transfer of forgein genes into intact maize cells with high-velocity microprojectiles. Proc. Natl. Acad. Sci. 85: 4305–4309.

Klein T M, Gradziel T, Fromm M E and Sanford J C (1988). Factor influencing gene delivery into *Zea mays* cells by high-velocity microprojectile. Bio/technology 6: 559–573.

Klein T M, Kornstein L, Sanford J C and Fromm M E (1989). Genetic transformation of maize cells by particle bombardment. Plant Physiol. 91: 440–444.

McMullen M D and finer J J (1990). Stable transformation of cotton and soybean embryogenic cultures via microprojectile bombardment (abstract). J. Cell Biochem. 14E: 285.

Meijer E G M, Schilperoort R A, Rueb S, van Os-Ruygrok P E and Hensgens L A M (1991). Transgenic rice cell lines and plants: expression of transferred chimaeric genes. Plan Mol. Biol. 16: 807–820.

Paszkowski J and Saul M (1988). Direct gene transfer to plants. In: Weissbach A, Weissbach (eds). Methods in Enzymology, vol 188: 668–685. New York: Academic Press.

Platt S G and Yang N-S (1987). Dot assay for neomycin phosphotransferase activity in crude cell extracts. Anal. Biochem. 162: 529–535.

Sambrook J, Fritsch E F, and Maniatis T: Molecular Cloning: A Laboratory Manual. 2nd edn. Cold Spring Harbor Laboratory, Cold Spring Harbor, N.Y. (1989).

Sanford J C, Klein T M, Wolf E D and Allen N (1987). Delivery of substances into cells and tissues using a particle bombardment process. Particle Science and Technology 5: 27–37.

Wang Y-C, Klein T M, Fromm M E, Cao J, Sanford J C and Wu R (1988). Transient expression of foreign genes in rice, wheat and soybean cells following particle bombardment. Plant Mol. Biol. 11: 433-

Vancanneyt, G., Schmidt, R., O'Connor, A., Sanchez, Willmitzer, L. and Rocha-Sosa, M. (1990). Construction of an intron-containing marker gene: Splicing of the intron in transgenic plants and its use in monitoring early events in Agrobacterium-mediated plant transformation. *Mol. Gen Genet,* 220, 245–250.

Horsch R B, Fry J E, Hoffmann N L, Eichholtz D, Rogers S G and Fraley, R T (1985). A simple and general method for transferring genes into plant. *Science* 227, 1229–1231.

Bevan M (1984). Binary Agrobacterium vectors for plant transformation. *Nucl. Acids Res.* 12, 8711–8721.

Herrera-Estrella L, Depicker A, Van Montagu M and Schell, J. (1983). Expression of chimaeric genes transferred into plant cells using a Ti plasmid derived vector. *Nature* 303, 209–213.

Simon, E. W. (1974). Phospholipid and plant membrane permeability. *New Phytol,* 73, 377–420.

Chen, Z., Qian, C., Qin, M., Xu, X., Xiao, Y., Lin, M. D. Z., Wu, S. and Huan, N. (1981 b). Recent advances in anther culture of rubber tree and sugarcane. In: Ann. Rep. Inst. Genetics Academia Sinica, Beijing, China, p. 103.

We claim:

1. A method of producing a protein from a genetically transformed Hevea plant which comprises:

i) transforming the plant tissue by insertion of a gene or gene fragment controlling the expression of a protein, and ii) regenerating a plant from said tissue, the genetically transformed Hevea plant expressing the protein in the latex that said plant produces, and iii) recovering the protein from said latex.

2. The method as claimed in claim 1, wherein the plant is *Hevea brasiliensis*.

3. The method as claimed in claims 1 or 2, wherein the insertion of the gene or gene fragment is performed using the Agrobacterium vector system.

4. The method as claimed in claims 1 or 2, wherein the insertion of the gene or gene fragment is performed using the particle gun method.

5. A method of producing a protein from a genetically transformed Hevea plant which comprises:

i) harvesting latex from the genetically transformed Hevea tree or plant, or a clone thereof, in a substantially continual manner which is non-destructive to said Hevea tree or plant, and ii) recovering the said protein from said latex.

* * * * *